(12) United States Patent
Yan et al.

(10) Patent No.: US 10,126,259 B2
(45) Date of Patent: Nov. 13, 2018

(54) RADIO FREQUENCY IDENTIFICATION (RFID) DEVICES FOR DETECTING VOLATILE SUBSTANCES

(71) Applicant: Ning Yan, Toronto, Ontario (CA)

(72) Inventors: Ning Yan, Toronto (CA); Lindsey Fiddes, Toronto (CA)

(73) Assignee: Ning Yan, Toronto (CA)

( * ) Notice: Subject to any disclaimer, the term of this patent is extended or adjusted under 35 U.S.C. 154(b) by 189 days.

(21) Appl. No.: 14/897,772

(22) PCT Filed: Jun. 10, 2014

(86) PCT No.: PCT/CA2014/050537
§ 371 (c)(1),
(2) Date: Dec. 11, 2015

(87) PCT Pub. No.: WO2014/197984
PCT Pub. Date: Dec. 18, 2014

(65) Prior Publication Data
US 2016/0161434 A1 Jun. 9, 2016

Related U.S. Application Data

(60) Provisional application No. 61/835,047, filed on Jun. 14, 2013.

(51) Int. Cl.
*H01L 23/58* (2006.01)
*G01N 27/12* (2006.01)
*G01N 33/00* (2006.01)

(52) U.S. Cl.
CPC ....... *G01N 27/126* (2013.01); *G01N 33/0073* (2013.01)

(58) Field of Classification Search
CPC .............. G01N 27/126; G01N 33/0073
USPC ........................................... 257/642
See application file for complete search history.

(56) References Cited

U.S. PATENT DOCUMENTS 5,574,377 A * 11/1996 Marquez-Lucero ........................ G01M 3/045 174/11 R
5,733,437 A * 3/1998 Baker ................... G01N 27/49 204/400
5,851,370 A * 12/1998 Maracas .......... G01N 27/44704 204/450

(Continued)

FOREIGN PATENT DOCUMENTS

WO WO 2013/180801 A1 12/2013

OTHER PUBLICATIONS

International Search Report and Written Opinion in International Application No. PCT/CA2014/050537.

(Continued)

*Primary Examiner* — Viet Q Nguyen
(74) *Attorney, Agent, or Firm* — Eric L. Lane; Green Patent Law

(57) ABSTRACT

A radio frequency identification device, for detecting at least one volatile substance, comprising an integrated circuit, an antenna electrically connected to said integrated circuit, and at least one conductor, between said integrated circuit and said antenna, preferably said at least one conductor comprises a conducting composite, preferably said conducting composite comprises a polymer matrix and a conductor.

9 Claims, 10 Drawing Sheets

Before swelling    After swelling
☐ polymer
● carbon black
⸱ sensing element
▴ biogenic amine

(56) References Cited

U.S. PATENT DOCUMENTS

| | | | | |
|---|---|---|---|---|
| 6,234,006 B1* | 5/2001 | Sunshine | G01N 33/0009 | 422/83 |
| 6,416,714 B1* | 7/2002 | Nova | B01J 19/0046 | 422/403 |
| 7,179,421 B1* | 2/2007 | Ho | G01N 27/126 | 422/50 |
| 7,189,360 B1* | 3/2007 | Ho | G01N 27/126 | 29/592.1 |
| 7,338,811 B2* | 3/2008 | Lai | B01J 19/0046 | 422/504 |
| 8,900,856 B2* | 12/2014 | Muller-Cohn | A01N 1/00 | 435/287.1 |
| 9,163,313 B2* | 10/2015 | Chiao | C23C 28/345 | |
| 2002/0142477 A1* | 10/2002 | Lewis | G01N 33/0031 | 436/151 |
| 2004/0194534 A1* | 10/2004 | Porter | G01N 29/022 | 73/24.01 |
| 2005/0150778 A1* | 7/2005 | Lewis | G01N 27/126 | 205/777.5 |
| 2006/0034731 A1* | 2/2006 | Lewis | G01N 27/121 | 422/88 |
| 2006/0199196 A1* | 9/2006 | O'Banion | B01L 3/545 | 435/6.16 |
| 2007/0211398 A1* | 9/2007 | Whitney | G06K 19/077 | 361/42 |
| 2011/0140703 A1* | 6/2011 | Chiao | G01N 27/403 | 324/438 |
| 2012/0116683 A1 | 5/2012 | Radislav et al. | | |
| 2012/0270205 A1 | 10/2012 | Patel et al. | | |
| 2013/0049932 A1* | 2/2013 | Baym | G06K 19/0723 | 340/10.1 |
| 2015/0116093 A1* | 4/2015 | Swager | G06K 19/0717 | 340/10.4 |
| 2015/0273737 A1* | 10/2015 | Chen | B29C 41/22 | 428/336 |
| 2016/0061830 A1* | 3/2016 | Elias | G01N 33/56911 | 435/5 |

OTHER PUBLICATIONS

Radislav et al. "Battery-free Radio Frequency Identification (RFID) Sensors for Food Quality and Safety" Journal of Agricultural and Food Chemistry Sep. 5, 2012 60 (35).

Radislav et al. "Multianalyte Chemical Identification and Quantitation Using a Single Radio Frequency Indentification Sensor" Analytical Chemistry 2007 79 (1), 45-51.

\* cited by examiner

Before swelling    After swelling

□ polymer
● carbon black
◂ sensing element
▴ biogenic amine

RADIO FREQUENCY IDENTIFICATION (RFID) DEVICES FOR DETECTING VOLATILE SUBSTANCES

FIELD OF THE INVENTION

The present inventions relates to RFID devices, processes for preparing said devices and the use of RFID devices for detecting volatile substances.

BACKGROUND OF THE INVENTION

RFID is an emerging technology despite first being used in the 1940's for "friend or foe" air plane identification. (M. R. Riebackm B. Crispo, *Pervasive Computing* 2006, January—, 62.) They are currently used to track goods, to access secure areas, to pay toll roads, to verify authenticity, and other information services. (M. & C. P. Roy Want, *RFID Explained: A Primer on Radio Frequency Identification*; First Edit.; 2006; B. Nathm F. Reynoldsm R. Want, *IEEE Pervasive Computing* 2006, 5, 22) RFID tags that contain a battery are referred to as active RFID tags. Battery-free RFID tags are referred to as passive RFID tags. Passive RFID tags are read by RFID tag readers, which send a radio frequency carrier signal that illuminates the RFID tag antenna creating an AC voltage. (M. & C. P. Roy Want, *RFID Explained: A Primer on Radio Frequency Identification*; First Edit.; 2006; P. Basl, 2011 The advantages of passive RFID tags are:

Passive tags do not include a battery, giving the device a long lifetime of twenty years or more;
Passive tags are much smaller than active tags. Hitachi's RFID "powder" is 50 µm by 50 µm in size;
Passive tags are typically less expensive than active tags.

Conventional sensor arrays known as 'electronic noses' are composed of arrays of sensors that act independently when exposed to chemical vapours; by analyzing the response of the array using a data analysis algorithm, such as principle component analysis, the chemicals can be identified. (B. J. Dolemanm E. J. Severinm N. S. Lewis, *Proceedings of the National Academy of Sciences of the United States of America* 1998, 95, 5442; Y. S. Kimm Y. S. Yangm S. Ham H. Pyom C. A. Choi, October 2005, 27, 585; N. S. Lewis, *Accounts of chemical research* 2004, 37, 663) Applications of vaporous chemical sensing vary including environmental monitoring, (R. I. Mackiem P. G. Strootm V. H. Varel, *Journal of Animal Science* 1998, 76, 1331; K. C. Persaudm S. M. Khaffafm P. I. Hobbsm R. W. Sneath, *Chemical senses* 1996, 21, 495) monitoring of foodstuffs (D. Hodginsm D. Sirnmonds, *The Journal of automatic chemistry* 1995, 17, 179; H. Searchm C. Journalsm A. Contactm M. Iopsciencem I. P. Address, *Pattern Recognition* 1993, 1493; M. C. Burlm B. J. Dolemanm A. Schafferm N. S. Lewis, *Sensors and Actuators B: Chemical* 2001, 72, 149), crime prevention and security (B. J. Dolemanm E. J. Severinm N. S. Lewis, *Proceedings of the National Academy of Sciences of the United States of America* 1998, 95, 5442; S. Maldonadom E. Garcia-Berriosm M. D. Woodkam B. S. Brunschwigm N. S. Lewis, *Sensors and Actuators B: Chemical* 2008, 134, 521), and monitoring in the medical field (A. P. Turnerm N. Magan, *Nature reviews. Microbiology* 2004, 2, 161). Like RFID tags, electronic nose detectors can be reliably used over days, weeks, or months if needed. However, unlike RFID tags, electronic noses are large, costly, require a power source, and cannot be easily integrated into packaging.

Food spoilage occurs as enzymes in bacteria decarboxylize amino acids to form biogenic amines. Biogenic amines are volatile organic substances that make up the toxic component of spoiled food and they are a direct indicator of food spoilage in meat, fish, wine, cheese and other food stuffs (C. Ruiz-Capillas and F. Jiménez-Colmenero, "Biogenic Amines in Meat and Meat Products," *Critical Reviews in Food Science and Nutrition*, vol. 44, no. 7-8, pp. 489-599, February 2005; R. J. Shakila, "Formation of Histamine and Other Biogenic Amines During Storage of Freshwater Fish Chunks," *Asian Fisheries Science*, vol. 15, pp. 1-6, 2002; G. Nouadje, N. Simeon, F. Dedieu, M. Nertz, P. Puig, and F. Couderc, "Determination of twenty eight biogenic amines and amino acids during wine aging by micellar electrokinetic chromatography and laser-induced fluorescence detection," *Journal of Chromatography A*, vol. 765, no. 2, pp. 337-343, March 1997; J. Karovičová and Z. Kohajdová, "Biogenic Amines in Food," *Biogenic Amines*, vol. 59, no. 1, 2005). Amine identification and quantification is challenging because underivatized amines are difficult to separate in common liquid and gas chromatography columns. Traditional analytical techniques such as gas chromatography coupled to mass spectrometry are not desirable because samples containing multiple amines must be derivatized to be sufficiently separated. In addition, this technique is costly, time consuming and requires a trained technician.

One emerging approach to performing analysis of volatile substance encompasses attaching an absorbing polymer film to an electronic sensor. This technique uses changes in the electronic properties of polymer sensing film to detect volatile chemicals as they absorb to the polymer film (R. a Potyrailo, A. Leach, W. G. Morris, and S. K. Gamage, "Chemical sensors based on micromachined transducers with integrated piezoresistive readout," *Analytical chemistry*, vol. 78, no. 16, pp. 5633-8, August 2006; R. A. Potyrailo, C. Surman, W. G. Morris, T. Wortley, M. Vincent, R. Diana, V. Pizzi, J. Carter, and G. Gach, "Lab-Scale Long-Term Operation of Passive Multivariable RFID Temperature Sensors Integrated Into Single-Use Bioprocess Components," *Sensors* (Peterborough, N.H.), pp. 16-19, 2011; I. Willner and E. Katz, "Integrating of Layered Redox Proteins and Conductive Supports for Bioelectronic Applications," *Angewandte Chemie* (International ed. in English), vol. 39, no. 7, pp. 1180-1218, 2000; R. a Potyrailo, "Polymeric sensor materials: toward an alliance of combinatorial and rational design tools?," *Angewandte Chemie* (International ed. in English), vol. 45, no. 5, pp. 702-23, January 2006; H. Yoon, S. H. Lee, O. S. Kwon, H. S. Song, E. H. Oh, T. H. Park, and J. Jang, "Polypyrrole Nanotubes Conjugated with Human Olfactory Receptors: High-Performance Transducers for FET-Type Bioelectronic Noses," *Angewandte Chemie* (International ed. in English), vol. 48, no. 15, pp. 2755-2758, 2009).

Using an impedance analyzer several parameters of the polymer film such as real and imaginary impedance spectra could be measured to identify and quantify different volatile substances. This method has had limited success detecting amines (T. D. Gibson, O. Prosser, J. N. Hulbert, R. W. Marshall, and P. Corcoran, "Detection and simultaneous identification of microorganisms from headspace samples using an electronic nose," *Sensors* (Peterborough, N.H.), vol. 44, pp. 413-422, 1997; G. A. Sotzing, J. N. Phend, R. H. Grubbs, and N. S. Lewis, "Highly Sensitive Detection and Discrimination of Biogenic Amines Utilizing Arrays of Polyaniline/Carbon Black Composite Vapor Detectors," *Communications*, no. 23, pp. 593-595, 2000; H. Search, C. Journals, A. Contact, M. Iopscience, and I. P. Address, "Performance of an electronic nose for quality estimation of ground meat," *Pattern Recognition*, vol. 1493, 1993). Furthermore, this technique requires using expensive Nafion film as the sensing film, needing a network analyzer to perform readings, where readings are position-dependant for analyte quantitation and relying on multivariate statistical analysis methods for identification and quantification.

Several prior art references discussing the use of RFID devices to detect substances include:

Potyrailo et al. ("Battery-free Radio Frequency Identification (RFID) Sensors for Food Quality and Safety", Journal of Agriculture and Food Chemistry, 2012, 60, 8535-8543);

Huang et al. ("A Passive Radio-Frequency pH-Sensing Tag for Wireless Food-Quality Monitoring", in press);

Potyrailo and Morris ("Multianalyte Chemical Identification and Quantitation Using a Single Radio Frequency Identification Sensor", Analytical Chemistry, 2007, 79, 45-51);

Smits et al. ("Development of Printed RFID Sensor Tags for Smart Food Packaging", IMCS 2012, 403-406);

U.S. Patent Application Publication No. 2012/0304741; and International Application Publication No. WO00/20852.

There exists a long felt need for a cost effective, sensitive and easy-to-use RFID device for the detection and quantitation of volatile substances including biogenic amines.

SUMMARY OF THE INVENTION

As used herein, the term "volatile substance" refers to at least one chemical substance, preferably possessing a vapour pressure at 25° C. of at least about 200 pascals, more preferably at least about 250 pascals and most preferably at least about 300 pascals. Examples of volatile substances include, but are not limited to, substituted and unsubstituted aliphatic hydrocarbons, aromatic hydrocarbons, alcohols, amines, ethers and esters branched ethers, linear and branched. More preferably, the volatile substances are selected from aliphatic and aromatic amines. Most preferably, the volatile substances may be biogenic amines.

As used herein, the term "conducting composite" refers to a polymer, preferably a polymer comprising at least one component which changes the electrical conductivity properties of the polymer. The conducting composite may also be in the form of ink.

As used herein, the term "conductor" refers to a substance, preferably at least one inorganic or organic electrical charge-carrying substance, such as, but not limited to, carbon nanotubes, carbon nanoparticles, graphite and carbon black powder. The particle size of the powder may range from about 200 nm to about 45 μm. More preferably the particle size ranges from about 250 nm to about 600 nm. Most preferably the particle size is about 500 nm. The particle size of the carbon nanoparticles is preferably less than about 500 nm. The carbon nanotubes may have an outside diameter of preferably about 10 to about 15 nm, an inside diameter of preferably about 2 to about 6 nm and a length of preferably about 0.1 to about 10 mm.

In one aspect of the invention, there is provided a radio frequency identification device, for detecting at least one volatile substance, comprising an integrated circuit, an antenna electrically connected to said integrated circuit, and at least one conductor, between said integrated circuit and said antenna, preferably said at least one conductor comprises a conducting composite, preferably said conducting composite comprises a polymer matrix and a conductor.

In another aspect of the invention, there is provided a radio frequency identification device, for detecting at least one amine, preferably a biogenic amine, comprising an integrated circuit, an antenna electrically connected to said integrated circuit, and at least one conductor, between said integrated circuit and said antenna, preferably said at least one conductor comprises a conducting composite, preferably said conducting composite comprises a polymer matrix and a conductor.

In another aspect of the invention, there is provided a process for preparing a radio frequency identification device, for detecting at least one volatile substance, comprising the steps of
1) providing a radio frequency identification device comprising an integrated circuit and an antenna;
2) optionally isolating a connection between the integrated circuit and the antenna; and
3) adding at least one conductor between the integrated circuit and the antenna, preferably said at least one conductor comprises a conducting composite, more preferably said conducting composite comprises a polymer matrix and at least one conductor.

In another aspect of the invention, there is provided a process for preparing a radio frequency identification device, for detecting at least one amine, preferably at least one biogenic amine, comprising the steps of
1) providing a radio frequency identification device comprising an integrated circuit and an antenna;
2) optionally isolating a connection between the integrated circuit and the antenna; and
3) adding at least one conductor between the integrated circuit and the antenna, preferably said at least one conductor comprises a conducting composite, more preferably said conducting composite comprises a polymer matrix, at least one conductor and at least one sensing element.

In another aspect of the invention, there is provided a use of a radio frequency identification device, for detecting at least one volatile substance, said device comprising an integrated circuit, an antenna, an electrical connection between said integrated circuit and said antenna, and at least one conductor, between said integrated circuit and said antenna, preferably said at least one conductor comprises a conducting composite, more preferably said conducting composite comprises a polymer matrix and a conductor.

In another aspect of the invention, there is provided a use of a radio frequency identification device, for detecting at least one amine, preferably at least one biogenic amine, said device comprising an integrated circuit, an antenna, an electrical connection between said integrated circuit and said antenna, and at least one conductor, between said integrated circuit and said antenna, preferably said at least one conductor comprises a conducting composite, more preferably said conducting composite comprises a polymer matrix, a conductor and a sensing element.

In one aspect of the invention, there is provided a modified radio frequency identification device, for detecting at least one volatile substance, comprising an integrated circuit, an antenna electrically connected to said integrated circuit, and at least one modifier, for modifying the electrical connection between said integrated circuit and said antenna, preferably said at least one modifier comprises a conducting composite, preferably said conducting composite comprises a polymer matrix and a conductor.

In another aspect of the invention, there is provided a modified radio frequency identification device, for detecting at least one biogenic amine, comprising an integrated circuit, an antenna electrically connected to said integrated circuit, and at least one modifier, for modifying the electrical connection between said integrated circuit and said antenna, preferably said at least one modifier comprises a conducting composite, preferably said conducting composite comprises a polymer matrix and a conductor.

In another aspect of the invention, there is provided a process for preparing a modified radio frequency identification device, for detecting at least one volatile substance, comprising the steps of
1) providing a radio frequency identification device comprising an integrated circuit and an antenna;
2) isolating a connection between the integrated circuit and the antenna; and
3) modifying the connection between the integrated circuit and the antenna with at least one modifier, preferably said at least one modifier comprises a conducting composite, more preferably said conducting composite comprises a polymer matrix and at least one conductor.

In another aspect of the invention, there is provided a process for preparing a modified radio frequency identification device, for detecting at least one amine, preferably at least one biogenic amine, comprising the steps of
1) providing a radio frequency identification device comprising an integrated circuit and an antenna;
2) optionally isolating a connection between the integrated circuit and the antenna; and
3) modifying the connection between the integrated circuit and the antenna with at least one modifier, preferably said at least one modifier comprises a conducting composite, more preferably said conducting composite comprises a polymer matrix, at least one conductor and at least one sensing element.

In another aspect of the invention, there is provided a use of a modified radio frequency identification device, for detecting at least one volatile substance, said device comprising an integrated circuit, an antenna, an electrical connection between said integrated circuit and said antenna, and at least one modifier, for modifying said electrical connection between said integrated circuit and said antenna, preferably said at least one modifier comprises a conducting composite, more preferably said conducting composite comprises a polymer matrix and a conductor.

In another aspect of the invention, there is provided a use of a modified radio frequency identification device, for detecting at least one biogenic amine, said device comprising an integrated circuit, an antenna, an electrical connection between said integrated circuit and said antenna, and at least one modifier, for modifying said electrical connection between said integrated circuit and said antenna, preferably said at least one modifier comprises a conducting composite, more preferably said conducting composite comprises a polymer matrix, a conductor and a sensing element.

In another aspect of the invention, the conducting composite further comprises a sensing element, preferably said sensing element is substantially insensitive to temperature, preferably substantially insensitive up to about 50° C. and preferably substantially insensitive to humidity changes.

In another aspect of the invention, a plurality of RFID devices may be arranged in an array of RFID devices for detecting multiple volatile substances. In one embodiment, the RFID device is a modified RFID device.

In one embodiment, the polymer used in the conducting composite may be a natural or synthetic homopolymer, co-polymer, grafted polymer or polymer blend, preferably the co-polymer comprises polar, heteroatomic, functionalized and the like monomer units. More preferably the polymer comprises a co-polymer selected from the group consisting of poly(n-vinyl pyrrolidone), poly(ethylene-co-vinyl acetate) (18% vinyl acetate) (PEVA), poly(ethylene-co-acrylic acid) (15% acrylic acid), poly(acrylic acid), poly(n-vinyl pyrrolidone-co-vinyl acetate) (60% n-vinyl pyrrolidone), poly(styrene-co-butadiene) (ABA block copolymer, PSB), poly(vinyl chloride, carboxylated), poly(vinyl chloride), poly(1,2-butadiene) (PBD), polyamide, phenoxy resin (PR), poly(methyl vinyl ether-co-maleic acid) (50:50, PMVEMA), poly(hydroxyl propyl cellulose), poly(ethylene-co-methacrylic acid) (12% methacrylic acid) and poly(cellulose propionate) and mixtures thereof. Preferably the co-polymer is selected from the group consisting of PEVA, PSB, PBD, PR and PMVEMA and mixtures thereof. More preferably the co-polymer is PEVA or PMVEMA. Most preferably the co-polymer is PEVA.

In an embodiment, the conducting composite may optionally contain a sensing element for sensing volatile substances. Preferably the sensing element is an organic compound sensitive to amines. More preferably the organic compound may be an organic acid or anhydride. Most preferably the organic compound is maleic anhydride.

The modified RFID device of the present invention may be prepared generally by providing an unmodified RFID device, isolating the electrical connection between the RFID device's integrated circuit and antenna, modifying the electrical connection by coating the connection with a conductive composite and curing the conductive composite to yield the modified RFID device.

In an alternate embodiment, the RFID device of the present invention may already be pre-modified with a conducting composite for use in detecting volatile substances.

In another embodiment, the RFID device of the present invention may exhibit an "on" or an "off" state. Preferably when exposed to an environment having an increasing concentration of a volatile substance, the device becomes unresponsive to a RFID device reader and enters an "off" state and removal of the volatile substance allows the RFID device to become responsive again, entering an "on" state.

Further and other aspects of the present invention will become apparent to those skilled in the art.

DETAILED DESCRIPTION OF THE PREFERRED EMBODIMENTS

Figure 1:
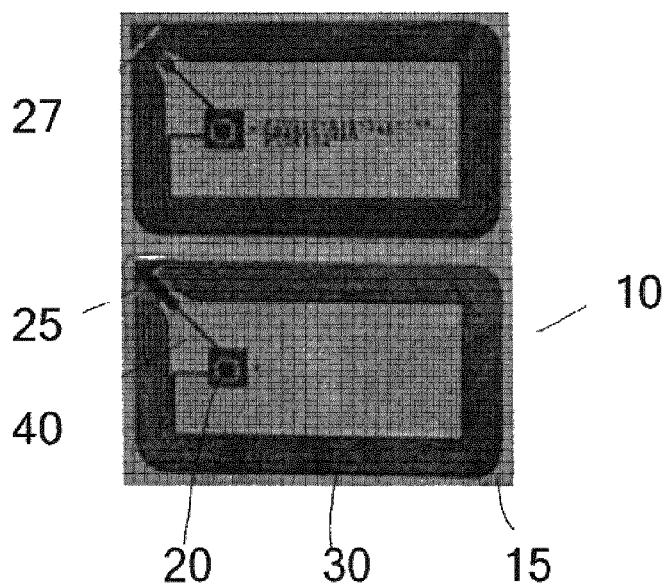
FIG. 1 is one embodiment of a modified RFID device of the present invention.

With reference to FIG. 1, the starting, unmodified RFID device 10 is preferably a commercially-available device and typically comprises an integrated circuit 20 connected to an antenna 30 and sandwiched between two plastic covers 15. The working frequency of an unmodified RFID device is typically about 13.5 MHz.

Access to the electrical connection 25 between the integrated circuit 20 and the antenna 30 on the RFID device 10 is achieved by removing one of the plastic covers 15 of the RFID device to expose a surface of the RFID device containing the integrated circuit 20 and the antenna 30. The electrical connection 25 between the integrated circuit 20 and the antenna 30 is typically a conductive silver paste 27. In some embodiments, the conductive silver paste 27 is isolated by applying, preferably, a dielectric silicone elastomer 40 to the exposed surface of the RFID device and curing the elastomer for about two hours at an elevated temperature, preferably from about 60° C. to about 80° C. A portion of the cured silicone covering the conductive silver paste connection is removed to expose the conductive silver paste and the remaining area of the RFID device remains masked by the silicone.

A solution of the conductive composite to be applied to the exposed conducive silver paste is prepared by dissolving a polymer in a suitable solvent, adding a conductor and optionally adding a sensing element. The polymer may be a natural or synthetic homopolymer or co-polymer, wherein the co-polymer comprises polar, heteroatomic, functionalized and the like monomer units. Preferably the polymer comprises a co-polymer selected from the group consisting of poly(n-vinyl pyrrolidone), poly(ethylene-co-vinyl acetate) (18% vinyl acetate) (PEVA), poly(ethylene-co-acrylic acid) (15% acrylic acid), poly(acrylic acid), poly(n-vinyl pyrrolidone-co-vinyl acetate) (60% n-vinyl pyrrolidone), poly(styrene-co-butadiene) (ABA block copolymer, PSB), poly(vinyl chloride, carboxylated), poly(vinyl chloride), poly(1,2-butadiene) (PBD), polyamide, phenoxy resin (PR), poly(methyl vinyl ether-co-maleic acid) (50:50, PMVEMA), poly(hydroxyl propyl cellulose), poly(ethylene-co-methacrylic acid) (12% methacrylic acid) and poly(cellulose propionate). Preferably the co-polymer is selected from the group consisting of PEVA, PSB, PBD, PR and PMVEMA. More preferably the co-polymer is PEVA or PMVEMA. Most preferably the co-polymer is PEVA. The solvent may be selected from solvents in which the polymer is soluble, preferably water, ethanol, chloroform, chlorobenzene or tetrahydrofuran (THF), more preferably chlorobenzene or chloroform and most preferably chlorobenzene. The conductor may be selected from an inorganic or organic electrical charge-carrying substance such as, but not limited to, graphite, carbon nanotubes, carbon nanoparticles and carbon black powder. Most preferably the conductor is carbon black powder. The particle size of the carbon black powder may range from about 200 nm to about 45 μm. More preferably the particle size ranges from about 250 nm to about 600 nm. Most preferably the particle size is about 500 nm. In certain embodiments, the optional sensing element comprises an organic compound sensitive to amines. More preferably the organic compound comprises an organic acid or anhydride. Most preferably the organic compound is maleic anhydride.

The solution of the conductive composite is added dropwise to the exposed conductive silver paste 27 of the RFID device 10 and heated to between about 50° C. and about 90° C. for about ten minutes to evaporate the solvent. This step can be repeated as necessary to obtain sufficient coating of the conductive silver paste by the conductive composite, as would be understood by a person of skill in the art. The operating frequency of the resultant modified RFID device increases from about 13.5 MHz to about 14.2 MHz.

Figure 2:
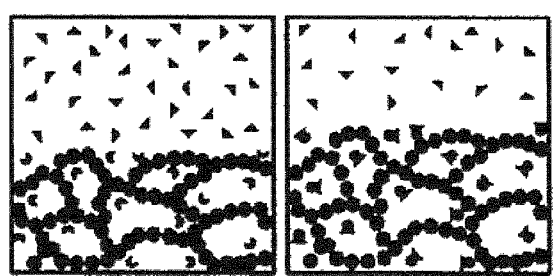
FIG. 2 is a schematic showing the conductive composite used in the modified RFID device of the present invention before and after swelling.

Adsorption of a volatile substance by the modified RFID device of the present invention can be achieved by exposing the device to sealed environment containing the volatile substance. Certain conductive composites preferentially adsorb certain volatile substance. For example, conductive composites comprising non-polar polymers, such as PEVA or poly(vinyl chloride) adsorb non-polar volatile substances, such as toluene, whereas conductive composites comprising polar polymer, such as poly(acrylic acid) or poly(methyl vinyl ether-co-maleic acid) adsorb water. With reference to FIG. 2, in the presence of a volatile substance, the conductive composite swells which alters the electrical properties of the modified RFID device.

In certain embodiments, the device may be inserted, for example, in food packaging either at the same time as the food is packaged to act as a continuous monitor of food freshness or at some point in the future to instantly assess the freshness of the packaged food. It is known in the art that as food spoilage occurs certain volatile biogenic amines such as, for example, putrescine, histamine, cadaverine, spermine and spermidine, are created as a consequence of the breakdown of the food by microorganisms. In one embodiment, a modified RFID device with a conductive composite comprising PEVA, carbon black and maleic anhydride can selectively adsorb one or more of these biogenic amines and its presence and quantity may be assessed using a RFID device reader known in the art.

Figure 12:
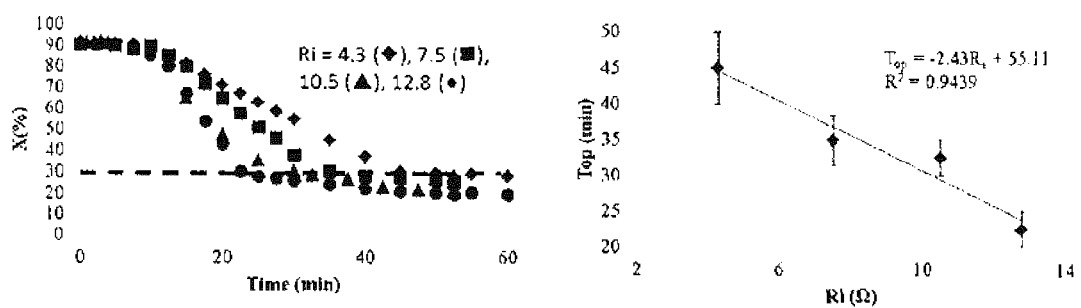
FIG. 12 is plot of length of time between the start of exposure of putrescine to a modified RFID device of the present invention until the device become inoperable as function of RFID device resistance.

The modified RFID device of the present invention may reversibly adsorb volatile substances so that the device may be reusable. Desorption of the adsorbed volatile substance is typically achieved by exposing the device to an environment that is free of the volatile substance previously adsorbed. With reference to FIG. 12, the modified RFID devices of the present invention may also behave in either an "on" or an "off" state. For example, when exposed to an increasing concentration of a volatile substance, the device becomes unresponsive to a RFID device reader, i.e. an "off" state. Removal of the volatile substance allows the RFID device to become responsive again, i.e. an "on" state. The time it takes a modified RFID device to turn off is about 25 to about 35 minutes when exposed to an about 1 M aqueous solution of an amine.

The modified RFID device of the present invention is a passive device and operates in a backscatter fashion as would be understood by a person of skill in the art: a RFID device reader powers the modified RFID device when the modified RFID device is in the device reader's electromagnetic field. The modified RFID device reflects the signal based on its radar cross section (RCS). The modified RFID device may change its RCS, including the amplitude and the phase of the signal, according to the impedance matching between the antenna and the integrated circuit.

In operation and without being bound by theory, when the modified RFID device of the present invention is not exposed to volatile substances, the impedance of the antenna best matched the impedance of the integrated circuit and the RCS is larger and the reflection is greater. When the modified RFID device of the present invention is exposed to volatile substances such as, for example, biogenic amines, the conducting composite swells which increases the resistance of the conductive composite resulting in an increase in the impedance of the integrated circuit. Because the impedance between the antenna and the integrated circuit becomes mismatched the RFID tag must increase the impedance of the antenna and this decreases the RCS resulting in a decrease in tag reflection and operating frequency. The ratio between these two states is called the differential coefficient of reflectivity, $\rho$. It can be calculated as (F. Terman, "Radio Engineers' Handbook." McGraw Hill Book Company, Inc., 1943):

$$\rho = \frac{\frac{Z_L}{Z_A} - 1}{\frac{Z_L}{Z_A} + 1} \qquad 1$$

where $Z_L$ is the load impedance and $Z_A$ is the antenna impedance. When the antenna impedance is purely resistive (F. Terman, "Radio Engineers' Handbook." McGraw Hill Book Company, Inc., 1943):

$$\rho = \sqrt{\frac{(R_L - R_r)^2 + X_L^2}{(R_L + R_r)^2 + X_L^2}} \qquad 2$$

where $R_L$ is the resistive part of the load, $R_r$ is the antenna radiation resistance and $X_L$ is the reactive part of the load. When the impedance of the antenna and the integrated circuit is matched, $R_L = R_r$ and the tag will absorb half of the incident power and re-radiate the remaining power, i.e. $\rho = 0.5$. When the modified RFID device of the present invention absorbs volatile substances such as, for example, biogenic amines, the resistance of the integrated circuit increases, less of the incident power is re-radiated and $\rho > 0.5$. When the antenna is mismatched the RCS is:

$$\sigma = \frac{\lambda^2}{4\pi} G^2 \rho^2 \qquad 3$$

and power re-radiated by the antenna is given by (H. Lehpamer, *RFID Design Principles*, 2nd ed. Norwood, Mass.: US Library of Congress, 2012):

$$S = \frac{P_\tau G^2 \sigma \lambda^2}{(4\pi)^\varepsilon R^4} \qquad 4$$

where $P_r$ is the reader transmitted energy, G is the gain of the tag antenna, $\sigma$ is the radar cross section, $\lambda$ is the wavelength of the tag antenna and R is the distance between the reader and the tag. S is expressed in $\mu$Watts or dB.

Figure 3:
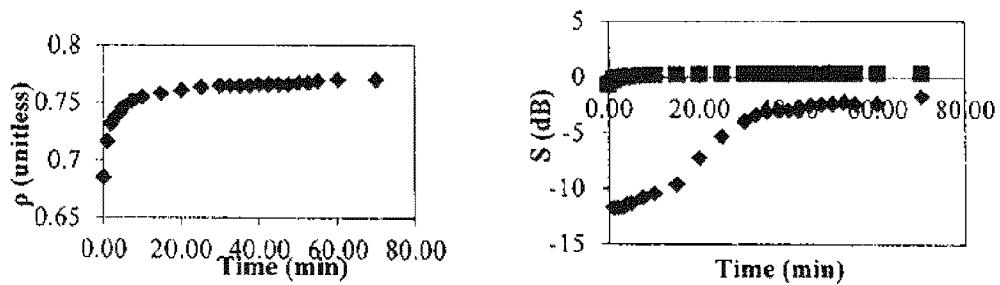
FIG. 3 is a plot of ρ as a function of time as the modified RFID device of the present invention is exposed to 1M putrescine FIG. 4 are plots of electrical properties of the modified RFID device of the present invention when exposed to 1M putrescine over 70 minutes.
Figure 4:
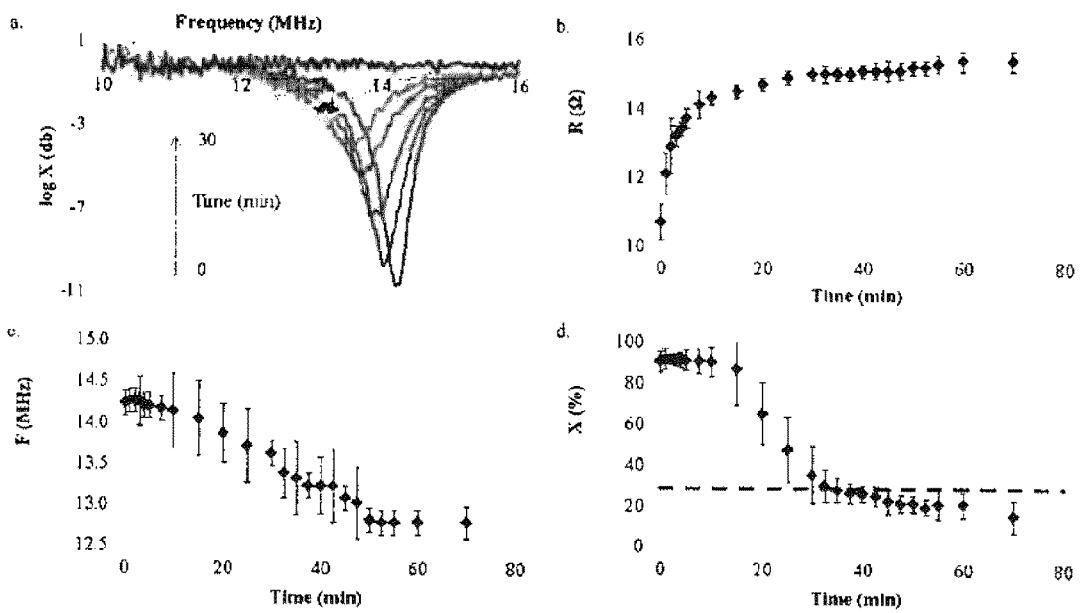

With reference to FIG. 3, $\rho$ plotted as a function of time as the modified RFID device is exposed to 1M putrescine using the resistance data shown in FIG. 4. The coefficient of reflection starts at above 0.5 (where impedance between the antenna and the integrated circuit is matched) and continues to increase due to an increase in the resistance of the integrated circuit. Using the plot of $\rho$ versus time, S versus time is calculated and plotted along with the experimental values of S. A large change in S is observed over the timescale of the experiment but only a modest change in S is calculated suggesting impedance of both the integrated circuit and the antenna is changing and that antenna impedance in these experiments is not purely resistive.

In certain embodiments, a plurality of modified RFID devices may be used for detecting a variety of volatile substances such as, for example, biogenic amines.

The following non-limiting examples are provided.

EXAMPLES

Materials

Ammonia hydroxide solution (28-30%), ethanol, toluene, chlorobenzene, tetrahydrofuran (THF), chloroform, carbon black (graphitized, particle size<500 nm), multi-wall carbon nanotubes (10-15 nm outside diameter, 2-6 nm inside diameter, 0.1-10 mm long) and carbon nanoparticles (<500 nm) were received from Sigma Aldrich (Oakville, ON) and used as received. The polymers in Table 1 were purchased from Scientific Polymer Products and used as received. Biogenic amine chloride salts of putrescine, histamine, cadaverine, spermine and spermidine were received from Sigma Aldrich (Oakville, ON) and used as received. Passive copper RFID tags (STMicroelectronics) with a nominal frequency of 13.56 MHz were purchased from Digi-Key Corporation (Thief River Falls, Minn.). The silicone elastomer kit was purchased from Dow Corning Corporation (Midland, Mich.) and used by mixing the monomer and the curing agent in a weight ratio of 10 to 1.

TABLE 1

Polymers used in RFID tag sensor array

| Sensor no. | Polymer |
|---|---|
| 1 | poly(n-vinyl pyrrolidone) |
| 2 | poly(ethylene-co-vinyl acetate), 18% vinyl acetate (PEVA) |
| 3 | poly(ethylene-co-acrylic acid), 15% acrylic acid |
| 4 | Poly(acrylic acid) |
| 5 | poly(n-vinyl pyrrolidone-co-vinyl acetate), 60% n-vinyl pyrrolidone |
| 6 | poly(styrene-co-butadiene), ABA block copolymer |
| 7 | poly(vinyl chloride), carboxylated |
| 8 | poly(vinyl chloride) |
| 9 | poly(1,2-butadiene) |
| 10 | polyamide resin |
| 11 | poly(acrylic acid) |
| 12 | phenoxy resin |
| 13 | poly(methyl vinyl ether-co-maleic acid), 50:50 |
| 14 | poly(hydroxyl propyl cellulose) |
| 15 | poly(ethylene-co-methacrylic acid), 12% methacrylic acid |
| 16 | poly(cellulose propionate) |

Example 1

The conducting composite was integrated onto the RFID device between the device's integrated circuit and antenna. A solution of 18 weight % carbon and 82 weight % polymer (see Table 1) was prepared for a total of 0.1 g in 15 mL of water, chloroform, or THF depending on the solubility of the polymer. The solution was sonicated for 3 h at room temperature. The unmodified RFID devices were received as a copper antenna sandwiched between two plastic sheets. The top plastic sheet was removed and the copper antenna was cleaned with acetone to remove any adhesive. The silver conductive paste that runs between the tag's integrated circuit and the antenna was modified with the conductive composite. First, the area was masked off by applying the silicone elastomer to the area identified above and curing for 2 h at 70° C. Once cured, the silicone was cut so that only the area with the conductive paste was exposed, and the remaining area was masked off with the silicone elastomer. Second, 10 µL of the conductive composite solution was pipetted onto the masked area and heated to 80° C. for 10 minutes to evaporate the solvent, leaving behind the conductive composite film. Modified RFID device resistance was measured with a digital multimeter (Mastercraft) and was found to increase from 1.2Ω to 3.0Ω upon addition of the first layer of conductive composite. Multiple layers of conductive composite were added to the tag to make tags with resistance 4.2, 7.5, 10.5, and 12.8Ω. All experiments were performed using tags with a resistance 10.5±0.5Ω unless stated otherwise. The resistance of RFID tag sensors is much lower than the resistance of electronic nose devices made from conducting polymer composites, which is typically on the order of MΩ. RFID tag devices operate at low resistance because the tags need to reach a critical DC voltage for microchip operation. Electronic noses made from conducting polymer composites operate at a high resistance to work near the percolation threshold to achieve the largest changes in resistance. After modification, the operating frequency of the RFID tags was found to increase from 13.56 MHz to 14.2 MHz.

Example 2

A solution of 18 weight % carbon black, 50 weight % PEVA and 32 weight % maleic acid was prepared for a total of 0.15 g in 15 mL of chlorobenzene. The solution was heated for 1 h in a 70° C. oven then sonicated for 1 h at room temperature. The unmodified RFID devices were received as a copper antenna sandwiched between two plastic sheets. The top plastic sheet was removed and the copper antenna was cleaned with acetone to remove any adhesive. The silver conductive paste that runs between the tag's integrated circuit and the antenna was modified with the conductive composite. First, the area was masked off by applying the silicone elastomer to the area identified above and curing for 2 hours at 70° C. Once cured the silicone was cut so that only the area with the conductive paste was exposed and the remaining area was masked off with the silicone elastomer. Second, 10 µL of the conductive composite solution was pipetted onto the masked area and heated to 80° C. for 10 minutes to evaporate the chlorobenzene. Modified RFID device resistance was measured with a digital multimeter and was found to increase from 1.2Ω to 3.0Ω upon addition of the first layer of conductive composite. Multiple layers of conductive composite were added to the device to make modified RFID devices with resistance 4.2, 7.5, 10.5, and 12.8Ω. All experiments were performed using modified RFID devices with a resistance 10.5±0.5Ω unless stated otherwise. After modification the optimal operating frequency of the RFID tags was found to increase from 13.56 MHz to 14.2 MHz.

Example 3

Figure 5A:
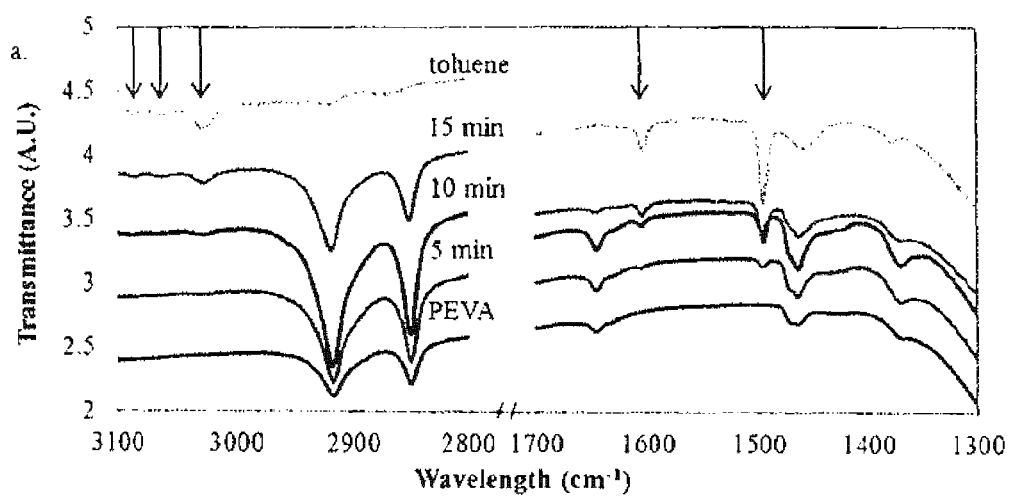
FIG. 5A is an FTIR spectrum of the modified RFID device of the present invention where the polymer is PEVA exposed to 377 ppm toluene for 5, 10 and 15 minutes, and toluene alone.

Conductive composite films were characterized on an attenuated total reflection (ATR) FTIR apparatus. Films of PEVA were cast on silicon wafers. The films were then attached to the inside lid of the environmental chamber and exposed to 377 ppm toluene for 15 minutes. ATR-FTIR measurements were conducted using a single reflection Ge ATR crystal accessory (PIKE Tech.) attached to a Vertex 70 FTIR spectrometer (Bruker Inc.) as described previously (J. Greenerm B. Abbasim E. Kumacheva, *Lab on a chip* 2010, 10, 1561). Spectra were obtained for the films before exposure, after 5, 10, and 15 min of exposure to toluene and for liquid toluene. FIG. 5A shows the FTIR spectra obtained. Peaks at 3094, 3071, and 3034 cm$^{-1}$ are C—H stretching for aromatic toluene. Peaks at 1607, and 1503 cm$^{-1}$ are C—C stretching for aromatic toluene. These aforementioned peaks are not in the PEVA spectrum but are shown to appear as the film is exposed to toluene confirming the analyte adsorption to the film.

Example 4

Figure 6:
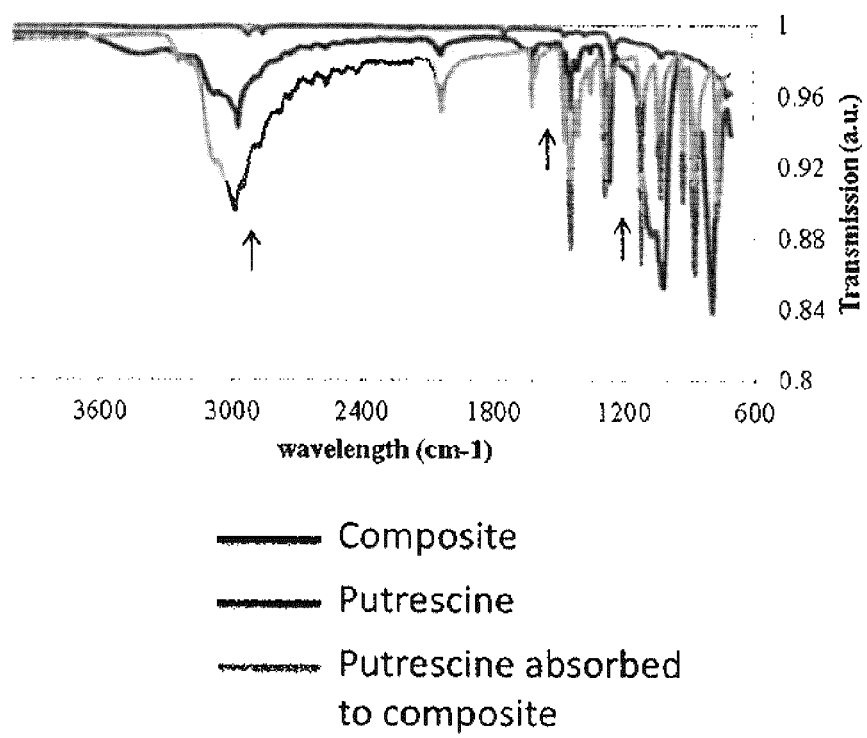
FIG. 6 is an FTIR spectrum of PEVA film, putrescine powder and PEVA film after exposure to 0.1 M putrescine for 30 minutes.

PEVA films were attached to the inside lid of a petri dish and exposed to 20 mL of 0.1M putrescine at 45° C. for 30 minutes. ATR-FTIR measurements were conducted using a single reflection Ge ATR crystal accessory (PIKE Tech.) attached to a Vertex 70 FTIR spectrometer (Bruker Inc.) as described previously J. Greener, B. Abbasi, and E. Kumacheva, "Attenuated total reflection Fourier transform infrared spectroscopy for on-chip monitoring of solute concentrations," *Lab on a chip*, vol. 10, no. 12, pp. 1561-6, June 2010. Spectra were obtained for the sensing film before exposure, after exposure and for the solid putrescine powder. FIG. 6 shows the FTIR spectra obtained. Peaks at 3000 (and above) and 1614 cm$^{-1}$ represent the primary NH bonds in putrescine. The peak at 1282 cm$^{-1}$ represents the CN bond. There was good overlap between the putrescine spectrum and the 'putrescine absorbed to film' spectrum to be confident that putrescine was adsorbed to the PEVA film.

Example 5

Figure 7A:
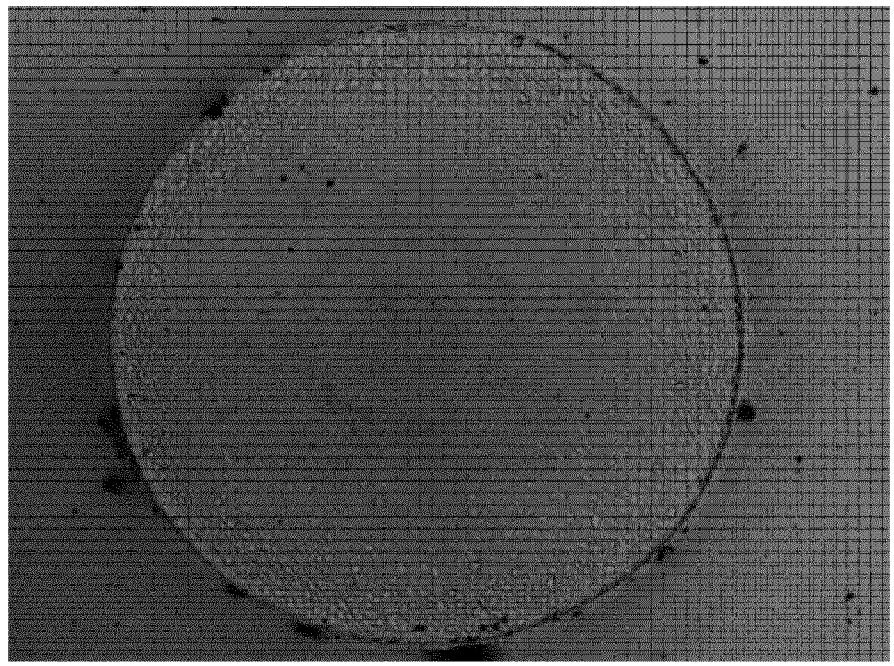
FIGS. 7A and 7B are pictures of bright field and fluorescent images of fluorescein-conjugated putrescine adsorbed to PEVA/maleic anhydride film.
Figure 7B:
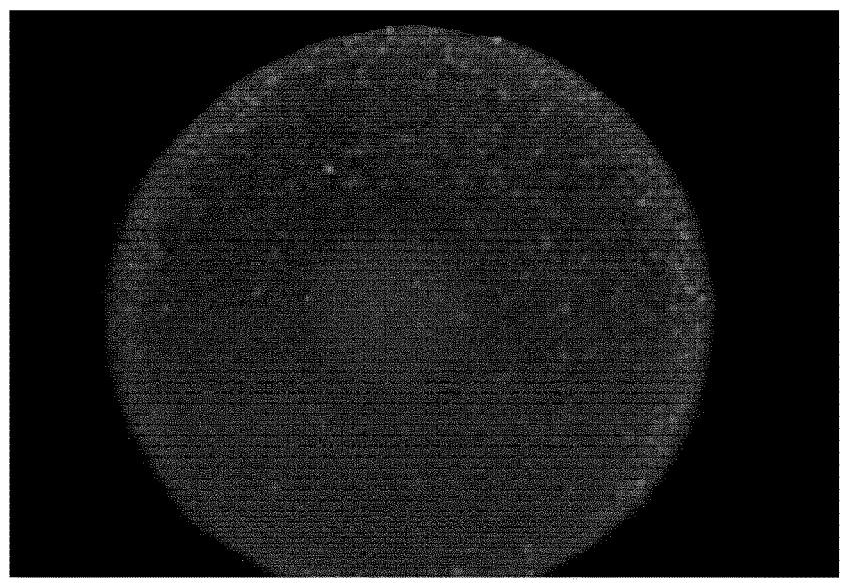

Bright field and fluorescent images of the films were taken to observe putrescine adsorption. A solution of 61% PEVA and 39% maleic anhydride for a total weight of 0.123 g in 15 mL of chlorobenzene was prepared. This material did not contain carbon black so that light could be transmitted through the film to achieve fluorescent images. The film was cast onto glass slides in a dot pattern and heated at 80° C. for 10 minutes. Fluorescein was added to a solution of 0.1M putrescine in 10 mM boric acid (pH 10.0) in a ratio of fluorescein to putrescine of 1:1. After 24 hours the solution was filtered. To perform adsorption experiments, 20 mL of the fluorescent putrescine solution were added to a petri dish and the film slide was taped to the inside lid of the petri dish. The petri dish was heated to 45° C. for 30 minutes so the putrescine could evaporate and adsorb to the film. After 30 minutes the film slide was removed from the petri dish and pictures of the film were collected using a microscope equipped with a fluorescent imaging module for 480/40 nm (Leica DM2000, Illinois, USA). FIGS. 7A and 7B shows the bright fields and fluorescent images of fluorescein labelled putrescine attached to the film. The fluorescent image shows the entire film was fluorescent but there are domains of more intense fluorescence in the film indicating that maleic anhydride phase separated from the PEVA to form more concentrated areas of maleic anhydride.

Example 6

An array of modified RFID device radio wave reflectance was collected from 10 to 16 MHz with a general purpose network analyzer (Agilent HPE8361A) as the device array was exposed to volatile solvent in air. Individual modified RED device resistance was measured with a digital multimeter. The network analyzer was equipped with a single coil copper antenna to collect the signal. Compressed air was bubbled through the solvent of interest to saturate the air, and a second compressed air tank was used to dilute the saturated air to achieve the desired concentration of solvent. The modified RED device array was affixed inside the lid humidity chamber. The network analyzer antenna was fixed at a distance of 5 mm from the lid of the humidity chamber, and each tag was read individually. The modified RFID device array was exposed to solvent vapour at a pressure of 5 PSI for 30 minutes at varying concentrations or cycled between solvent vapour and air for 5 minutes each. Experiments were run in triplicate to generate error bars.

Example 7

Example 6 was repeated using solutions of biogenic amines. The network analyzer was equipped with a single coil copper antenna to collect the signal. Solutions of biogenic amines (20 mL in 10 mM boric acid, pH 10.0) were placed in a petri dish and heated to 45° C. The modified RFID device was affixed to the inside lid of the petri dish. The network analyzer antenna was fixed at a distance of 5 mm from the lid of the petri dish. Tag reflectance and film resistance were measured over 70 minutes unless otherwise stated. Experiments were run in triplicate to generate error bars.

Example 8

Figure 7C:
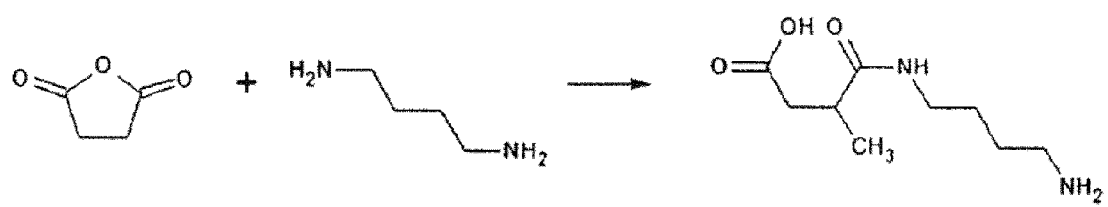
FIG. 7C is a schema of maleic anhydride binding with putrescine

A sensing film composed of PEVA, carbon black and maleic anhydride was used to detect biogenic amines produced during bacterial food spoilage. PEVA was selected as the polymer base because in previous studies it was shown to not swell greatly with water which is present in all samples in large quantities (M. C. Lonergan, E. J. Severin, B. J. Doleman, S. A. Beaber, R. H. Grubbs, and N. S. Lewis, "Array-Based Vapor Sensing Using Chemically Sensitive, Carbon Black-Polymer Resistors," *Society*, vol. 4756, no. 14, pp. 2298-2312, 1996). Carbon black was added to the film to ensure the film was conductive. Maleic anhydride was used as the sensing material in the film; maleic anhydride binds to primary amines to form a stable amide bond at neutral to basic pH (P. J. G. Butler, J. I. Harris, B. S. Hartley, and R. Leberman, "Reversible blocking of peptide amino groups by maleic anhydride," *Biochemistry Journal*, vol. 103, p. 78P, 1967). FIG. 2 shows an illustration of putrescine adsorbing to the composite. FIG. 7C shows the scheme of putrescine binding to maleic anhydride.

Example 9

Modified RFID devices were tested over a period of time as they were exposed to vaporous solutions of amines in water. During exposure, device resistance, R, was measured as well as tag reflectance from 10 to 16 MHz. The tag reflectance properties measured were the peak frequency, F, at which the maximum amount of radio waves are reflected and the amount of radio waves reflected, X, expressed as a log value (in decibels, dB) or a percentage of the radio waves reflected. FIG. 4 shows the modified RFID device's response when exposed to 1M putrescine for 70 minutes. As the device was exposed to volatile water and putrescine the conductive composite on the device swells. This swelling increases the distance between the carbon black particles in the sensing film which causes the resistance of the film to increase. The increase in the device's resistance causes changes to the radio wave reflectance spectrum; the frequency that reflected the most radio waves decreases and the percentage of radio waves reflected at the peak frequency decreased. When the modified RFID device reflects only 30% or less of the inputted radio waves it is considered inoperable (tag cannot be read with a conventional tag reader). Using this device it took 32.5±2.5 minutes for 1M putrescine to render the modified RFID device inoperable. At this time the tag resistance was 14.9±0.2Ω.

Example 10

Figure 5B:
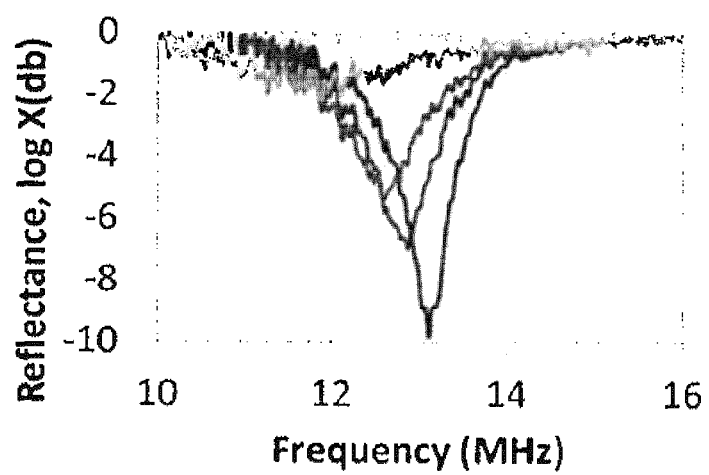
FIG. 5B is a plot showing changing reflectance properties of the modified RFID device of the present invention where the conductive composite comprises PEVA and carbon black when exposed to 373 ppm toluene for 30 minutes.

To demonstrate how the properties of an individual tag changes over time, modified RFID device containing PEVA/carbon black conductive composite was exposed to 373 ppm toluene for 30 minutes. FIG. 5B shows how the radiofrequency on an individual RFID tag changes as it is exposed to a volatile chemical. The signal is plotted as the power of the radiowaves reflected (S, in db) versus the frequency (MHz) as found by the network analyzer. Toluene adsorbs into the PEVA/carbon black conductive composite, which causes the composite to swell, the distance between carbon black particles to increase, and the resistance in the film to increase. As a result, the number of radiowaves the antenna reflects decreases, and the peak frequency at which the antenna reflects shifts to a lower frequency as seen in FIG. 5B. Modified RFID device frequency changed from 10.5Ω to 20.9Ω. This sensor is particularly sensitive to toluene so after 30 minutes the antenna still had low resistance, but the modified RFID device could no longer reflect the incoming signal and was incommunicative.

Example 11

Figure 8:
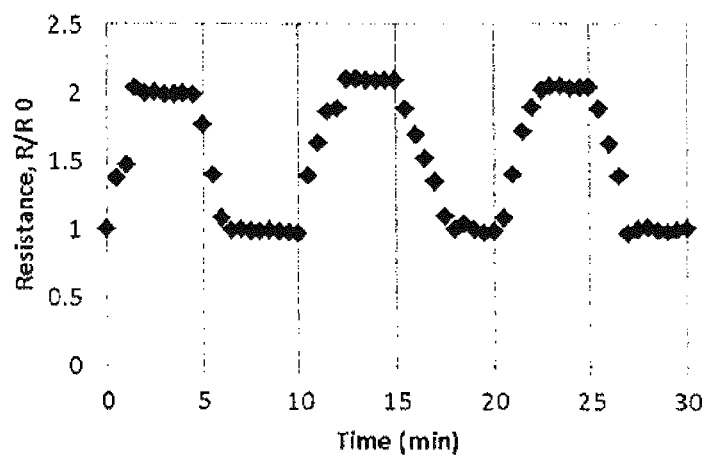
FIG. 8 are plots of the change in nominal frequency of a modified RFID device of the present invention where the polymer is PEVA after exposure to 37.3 ppm toluene for 0, 10 and 20 minutes, then air without toluene for 5, 15 and 25 minutes.

To demonstrate that the adsorption of vapour to the conductive composites is reversible, a modified RFID device containing PEVA was exposed to a cycle of 37.3 ppm toluene at 5 PSI for 5 minutes then to air at 5 PSI for 5 minutes. During that time, device frequency, reflectance, and resistance were monitored and are shown in FIG. 8. Over time the modified RFID device frequency changed from 14.2 to 13.2 MHz linearly with exposure to toluene and relaxed back to its original frequency after 2 minutes of exposure to air. Modified RFID device reflectance does not initially decrease. Upon exposure, device reflectance properties do not change in the first 2 minutes, then the reflectance decreases from 90% of radiowaves reflected to 60% of radiowaves reflected within the first 5 minutes of exposure. Once exposed to air, the modified RFID device's reflectance increases back to its original frequency after 2 minutes. Device resistance increases linearly over the first 2.5 minutes of exposure to toluene and decreases over 2 minutes upon exposure to air.

Example 12

Figure 9:
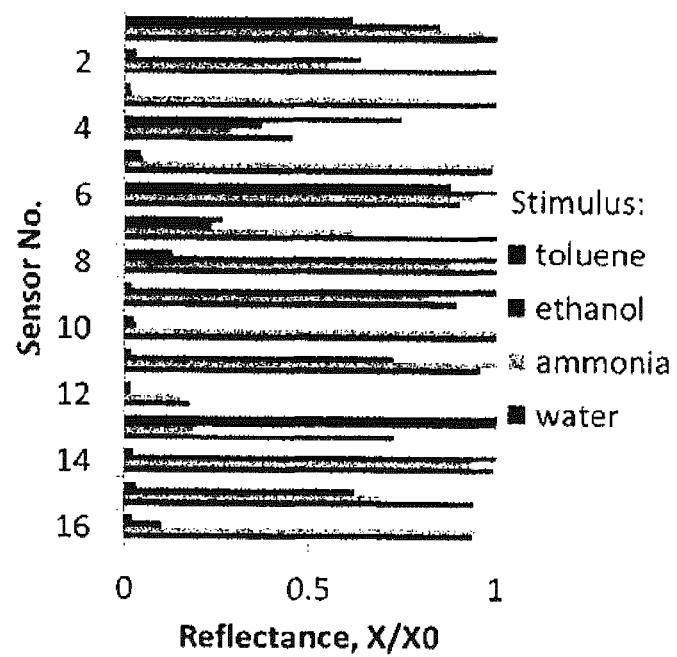
FIG. 9 are plots of the change in reflectance of an array a modified RFID device of the present invention when exposed to four different volatile substances.

An array of modified RFID devices with an initial resistance of 10.5Ω was prepared using the polymers from Table 1. The array was exposed to water (31.3 ppm), ammonia (151 ppm), ethanol (77.5 ppm), or toluene (37.3 ppm) for 5 minutes at 5 PSI and intermittently exposed the array to air at 5 PSI for 10 minutes. FIG. 9 shows how the array responded to the four analytes of interest. The figure shows the change in device reflectance ($S/S_0$) after it has been exposed to the vapour for 5 minutes. Non-polar polymers such as PEVA and poly(vinyl chloride) adsorbed toluene and decreased the amount of signal reflected, while polar polymers such as poly(acrylic acid) and poly(methyl vinyl ether-co-maleic acid) adsorbed water preferentially.

Example 13

Figure 10:
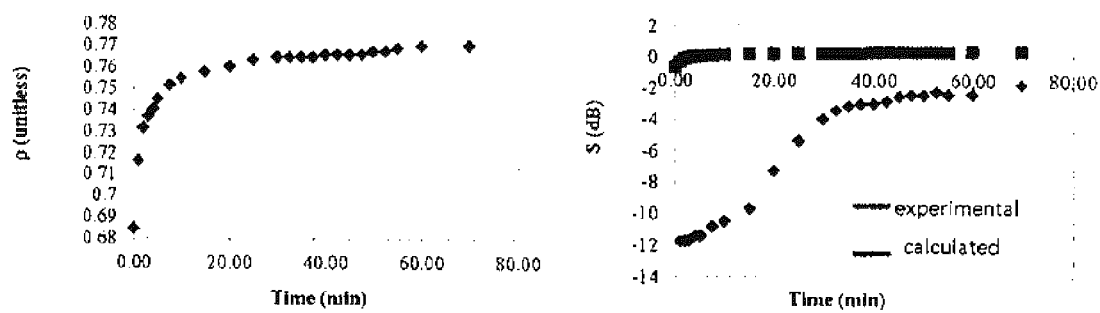
FIG. 10 are plots of coefficient of reflection versus time for a modified RFID device of the present invention after exposure to 1 M putrescine and experimental and calculated power of backscattered radio waves versus time under the same conditions.
Figure 11A:
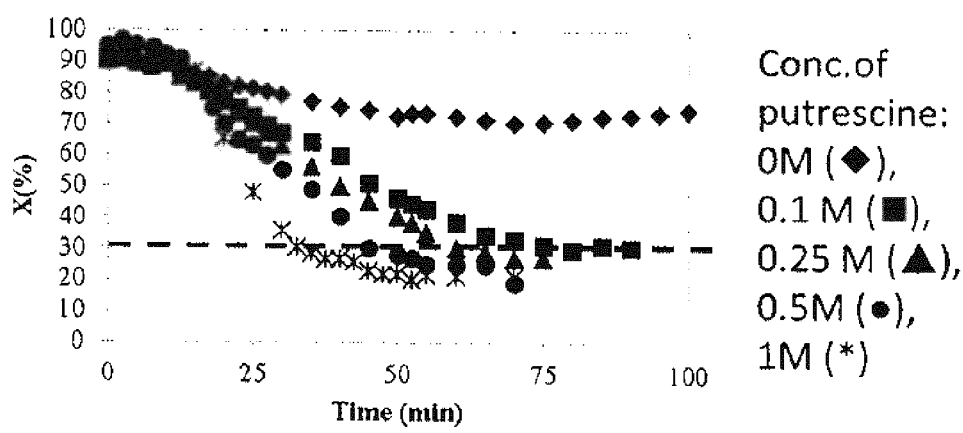
FIG. 11A is a plot of the change in the percentage of radio waves reflected over time after exposure of a modified RFID device of the present invention to varying concentrations of putrescine.
Figure 11B:
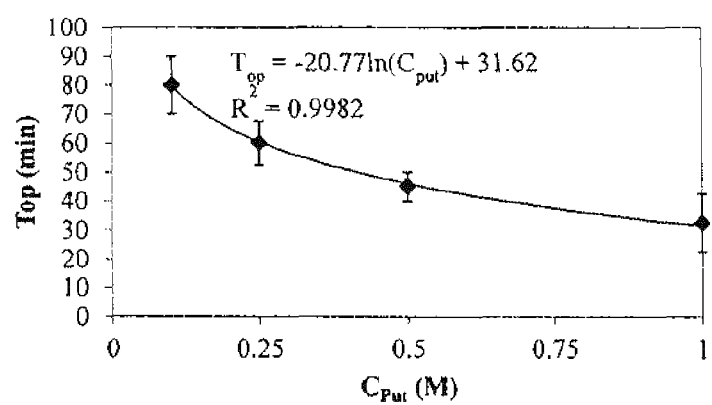
FIG. 11B is a plot of the length of time between the start of exposure of putrescine to a modified RFID device of the present invention until the device become inoperable as a function of concentration of putrescine.

Modified RFID devices as described above were exposed to different concentrations of putrescine, $C_{put}$, 0 (pure water), 0.1, 0.25, 0.5 and 1 M putrescine. FIG. 10 shows the plot of tag reflectance over time for each experiment. In general as putrescine concentration increases the steeper the decrease in device reflectance. FIG. 10 also shows the plot of measured time, $T_{op}$, versus putrescine concentration. FIG. 11B shows that as putrescine concentration increases, $T_{op}$ decreases and the relationship appears to be a logarithmic decay following the equation $T_{op}=-20.77 \ln(C_{put})+31.62$ and an $R^2$ value of 0.9982. Modified RFID devices were continuously monitored and resistance data were recorded to the device's own memory such that calibration curves could determine local concentration of volatile molecules.

Example 14

As in the examples described above, when the modified RFID device that was initially 10.7Ω was exposed to 1M putrescine it stopped communicating at 32.5 minutes; at that time resistance was 14.9Ω. To test the dependence of device resistance to $T_{op}$, modified RFID devices with an initial resistance, $R_i$, of 4.2, 7.5, 10.7 and 12.8Ω were exposed to 1M putrescine. FIG. 11A shows the plot of device reflectance versus time for each experiment. In general as device initial resistance increases the steeper the decrease the device reflectance. FIG. 12 also shows the plot of $T_{op}$ versus device resistance. As device resistance increases so does $T_{op}$, and the relationship appears to be linear following the equation $T_{op}=-2.43Ri+55.11$ with an $R^2$ value of 0.94.

Example 15

Figure 13:
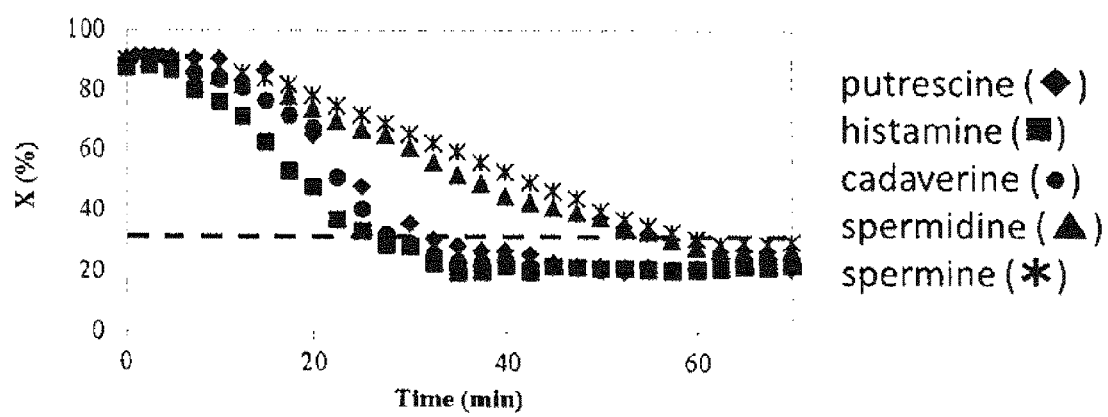
FIG. 13 is a plot of plot of tag reflectance versus time for a modified RFID device of the present invention when exposed to 1 M solutions of amines.

Biogenic amines produced during food spoilage are putrescine, histamine, cadaverine, spermidine and spermine. The amounts of these amines are used to calculate the biogenic amine index. The biogenic amine index, BAI, is calculated as: BAI=(mg kg$^{-1}$ histamine+mg kg$^{-1}$ putrescine+mg kg$^{-1}$ cadaverine)/1+mg kg$^{-1}$ spermine+mg kg$^{-1}$ spermidine (J. Karovičová, and Z. Kohajdová, "Biogenic Amines in Food," *Biogenic Amines*, vol. 59, no. 1, 2005). If the BAI value is greater than 10 then the sample is said to have a loss in quality. Modified RFID devices with an average initial resistance of 10.5Ω were exposed to 1M solutions of each of the five biogenic amines listed above. FIG. 13 shows the plot of tag reflectance versus time for each experiment. In all cases the amine was able to swell the modified RFID device conductive composite such that the device was no longer communicative. The modified RFID device was most sensitive to histamine only taking 27.5 minutes to become inoperable, followed by cadaverine (30 minutes), putrescine (32.5 minutes), spermidine (57.5 minutes) and spermine (62.5 minutes).

Example 16

RFID devices working at 13.56 MHz frequency were coated by conductive fillers (carbon nanoparticles (CNP), carbon nanotubes (MWCNT) and maleic anhydride grafted carbon nanotubes (g-MWCNT)), PEVA and maleic anhydride at weight ratios 18%/32%/50%. The amount of maleic anhydride grafted carbon nanotubes was adjusted to reach 18% by weight of the carbon nanotubes. Mixtures were dissolved in 15 mL of dichlorobenzene and sonicated for 1 hour at room temperature to ensure homogeneity. The RFID device final resistivity was about 5.0Ω.

Example 17

Figure 14:
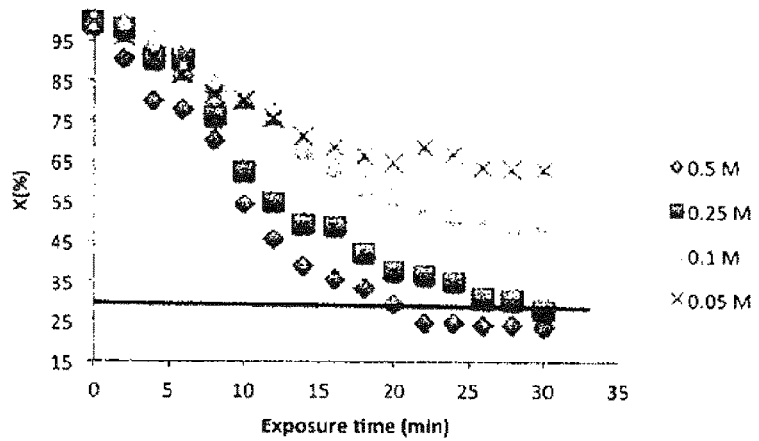
FIG. 14 is a plot of the reflected signal by a carbon nanoparticle/PEVA/maleic anhydride modified RFID device exposed to 0.5 M, 0.25 M, 0.1 M and 0.05 M putrescine over 30 min.
Figure 15:
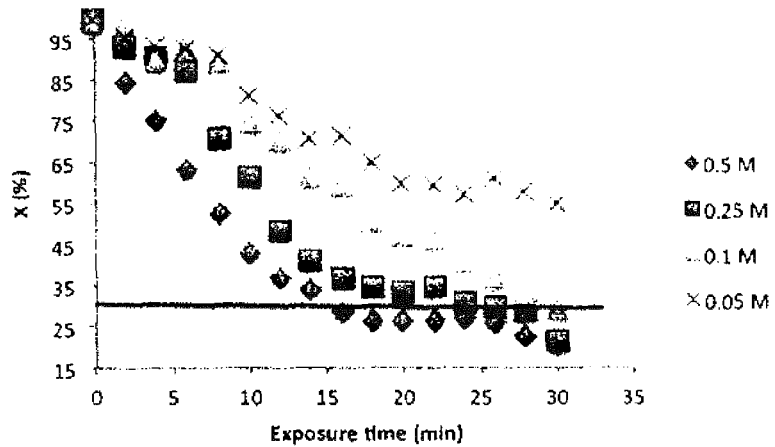
FIG. 15 is a plot of the reflected signal of a multi-walled carbon nanotube/PEVA/maleic anhydride modified RFID device exposed to 0.5 M, 0.25 M, 0.1 M and 0.05 M putrescine over 30 min.
Figure 16:
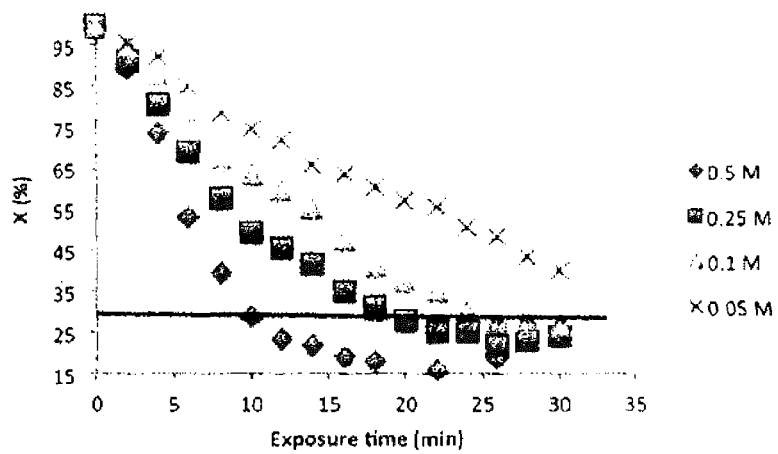
FIG. 16 is a plot of the reflected signal of maleic anhydride-grafted multi-walled carbon nanotube/PEVA modified RFID device exposed to 0.5 M, 0.25 M, 0.1 M and 0.05 M putrescine over 30 min.

A general Purpose Network Analyzer (PNA) working under frequencies from 10 MHz and 67 GHz was used to monitor RFID devices of Example 16 under exposure of putrescine. Results are contained in FIGS. 14-16. The results showed enhanced sensitivity for detection by the nanoparticles, nanotubes and grafted nanotubes.

Example 18

An ink solution containing 50% PEVA, 32% maleic anhydride and 18% carbon black (particle size of about 200 nm) to a total weight of 0.015 g in 15 mL of chlorobenzene was prepared. The solution was sonicated for 1 hour at room temperature then filtered using a 0.45 micro pore size syringe filter. The ink was jetted on a piezoelectric Dimatix DMP2800 inkjet printer (DMP cartridge, 21.5 mm nozzle diameter, 254 mm nozzle spacing, 16 nozzles).

The scope of the claims should not be limited by the preferred embodiments set forth in the examples, but should be given the broadest interpretation consistent with the description as a whole.

The invention claimed is:

1. A radio frequency identification device for detecting at least one volatile substance, comprising:
   an integrated circuit, an antenna electrically connected to said integrated circuit, and at least one conductor between said integrated circuit and said antenna, said at least one conductor comprising a conducting composite, said conducting composite comprising a polymer matrix and a conductive material, wherein the polymer matrix comprises a co-polymer selected from the group consisting of poly(n-vinyl pyrrolidone), poly(ethylene-co-vinyl acetate) (18% vinyl acetate) (PEVA), poly (ethylene-co-acrylic acid) (15% acrylic acid), poly (acrylic acid), poly(n-vinyl pyrrolidone-co-vinyl acetate) (60% n-vinyl pyrrolidone), poly(styrene-co-butadiene) (ABA block copolymer, PSB), poly(vinyl chloride, carboxylated), poly(vinyl chloride), poly(1,2-butadiene) (PBD), polyamide, phenoxy resin (PR), poly(methyl vinyl ether-co-maleic acid) (50:50, PMVEMA), poly(hydroxyl propyl cellulose), poly(ethylene-co-methacrylic acid) (12% methacrylic acid) and poly(cellulose propionate).

2. The device of claim 1 wherein the co-polymer is selected from PEVA or PMVEMA.

3. The device of claim 1 wherein the co-polymer is PEVA.

4. The device of claim 1 wherein the conductive material is selected from the group consisting of graphite, carbon nanotubes, carbon nanoparticles and carbon black powder, said carbon black powder having a particle size of about 200 nm to about 45 um.

5. The device of claim 4 wherein the conductive material is carbon black powder having a particle size of about 250 nm to about 600 nm.

6. The device of claim 4 wherein the conductive material is carbon black powder having a particle size of about 500 nm.

7. The device of claims 1 or 4 wherein the conducting composite further comprises at least one sensing element and the at least one sensing element is maleic anhydride.

8. The device of claim 4 wherein the carbon nanoparticles have a particle size less than about 500 nm.

9. The device of claim 4 wherein the carbon nanotubes have an outer diameter of about 10 to about 15 nm, an inside diameter of about 2 to about 6 nm and a length of about 0.1 to about 10 nm.

* * * * *